US010751017B2

United States Patent
Odry et al.

(10) Patent No.: US 10,751,017 B2
(45) Date of Patent: Aug. 25, 2020

(54) MODULAR AUTOMATED SCORING SYSTEM FOR TBI ASSESSMENT

(71) Applicant: Siemens Healthcare GmbH, Erlangen OT (DE)

(72) Inventors: Benjamin L. Odry, West New York, NJ (US); Hasan Ertan Cetingul, Baltimore, MD (US)

(73) Assignee: Siemens Heatlhcare GmbH, Erlangen (DE)

( * ) Notice: Subject to any disclaimer, the term of this patent is extended or adjusted under 35 U.S.C. 154(b) by 961 days.

(21) Appl. No.: 14/741,834

(22) Filed: Jun. 17, 2015

(65) Prior Publication Data
US 2016/0367209 A1  Dec. 22, 2016

(51) Int. Cl.
*A61B 5/00*  (2006.01)
*A61B 6/00*  (2006.01)
(Continued)

(52) U.S. Cl.
CPC .......... *A61B 6/501* (2013.01); *A61B 5/0042* (2013.01); *A61B 5/055* (2013.01); *A61B 6/037* (2013.01);
(Continued)

(58) Field of Classification Search
CPC ....... A61B 6/501; A61B 5/0042; A61B 5/055; A61B 6/037; A61B 6/5217; A61B 6/032;
(Continued)

(56) References Cited

U.S. PATENT DOCUMENTS 9,265,441 B2 * 2/2016 Pereira .................. A61B 5/055
2014/0081658 A1 3/2014 Irving et al.
(Continued)

FOREIGN PATENT DOCUMENTS

CN  103717129 A  4/2014

OTHER PUBLICATIONS

Lewine, Jeffrey David, et al. "Objective documentation of traumatic brain injury subsequent to mild head trauma: multimodal brain imaging with MEG, SPECT, and MRI." The Journal of head trauma rehabilitation 22.3 (2007): 141-155.*
(Continued)

*Primary Examiner* — Joel Lamprecht (57) ABSTRACT

A computer-implemented method for generating an assessment of traumatic brain injury (TBI) includes a TBI assessment computer receiving structural imaging data acquired by performing a structural imaging scan on an individual and generating a structural imaging score based on the structural imaging data. The TBI assessment computer receives functional imaging data acquired by performing a functional imaging scan on the individual and generates a functional imaging score based on the functional imaging data. The TBI assessment computer also receives diffusion imaging data acquired by performing a diffusion imaging scan on the individual and generates a diffusion imaging score based on the diffusion imaging data. Based on the structural imaging score, the functional imaging score, and the diffusion imaging score, the TBI assessment computer generates a TBI assessment score.

20 Claims, 6 Drawing Sheets

(51) Int. Cl.
  *A61B 6/03*   (2006.01)
  *A61B 5/055*  (2006.01)
  *G06T 7/00*   (2017.01)
  *G16H 50/30*  (2018.01)
  *G16H 30/40*  (2018.01)

(52) U.S. Cl.
  CPC .......... *A61B 6/5217* (2013.01); *G06T 7/0012* (2013.01); *G16H 30/40* (2018.01); *G16H 50/30* (2018.01); *A61B 6/032* (2013.01); *G06T 2207/10088* (2013.01); *G06T 2207/10104* (2013.01); *G06T 2207/30016* (2013.01); *G06T 2207/30096* (2013.01)

(58) Field of Classification Search
  CPC ......... G06T 7/0012; G06T 2207/10088; G06T 2207/30096; G06T 2207/30016; G06T 2207/10104
  See application file for complete search history.

(56) References Cited

U.S. PATENT DOCUMENTS

| | | | |
|---|---|---|---|
| 2014/0289172 A1* | 9/2014 | Rothman | G06N 5/04 706/11 |
| 2015/0018664 A1* | 1/2015 | Pereira | A61B 5/055 600/410 |

OTHER PUBLICATIONS

McAllister, Thomas W., et al. "Neuroimaging findings in mild traumatic brain injury." Journal of Clinical and Experimental Neuropsychology 23.6 (2001): 775-791.*

Kou, Z., et al. "Susceptibility weighted imaging complements to diffusion tensor imaging in traumatic brain injury." Neuroimage 47.1 (2009): S68.*

* cited by examiner

Fig. 1

| Scoring Type | Sequence | Lesion type | NULL = 0 | MILD = 1 | MODERATE = 2 | SEVERE = 3 | AMS |
|---|---|---|---|---|---|---|---|
| $S_1$ | T1 / T2-weighted | T2 hyper intensities | absent | [1;3] | [4;6] | [7,..[ | 6 |
|  |  | Other T1 / T2-weighted findings | absent | [1;3] | [4;6] | [7,..[ |  |
| $S_2$ | SWI / FLAIR | Lesions / mass | absent | [1;3] | [4;6] | [7,..[ | 3 |
| $S_3$ | PET | Lesions / mass | absent | [1;3] | [4;6] | [7,..[ | 3 |
| $S_4$ | mcDESPOT | DVF | Normal | < 1 STD | Between 1 and 2 STD | Greater than 2 STD | 3 |

| Evolution compared to normal | Less than 1 STD | Between 1 and 2 STD | Between 2 and 3 STD | More than 3 STD |
|---|---|---|---|---|
| Tract Length | 0 (normal) | 1 (MILD) | 3 (MODERATE) | 5 (SEVERE) |
| Number of tracts | 0 (normal) | 1 (MILD) | 3 (MODERATE) | 5 (SEVERE) |
| Symmetry of connectivity | 0 (normal) | 1 (MILD) | 3 (MODERATE) | 5 (SEVERE) |
| FA assessment | 0 (normal) | 1 (MILD) | 3 (MODERATE) | 5 (SEVERE) |
| MD assessment | 0 (normal) | 1 (MILD) | 3 (MODERATE) | 5 (SEVERE) |

MODULAR AUTOMATED SCORING SYSTEM FOR TBI ASSESSMENT

TECHNICAL FIELD

The present disclosure relates generally to a modular and automated scoring system for traumatic brain injury (TBI) assessment which utilizes structural, functional, and diffusion data gathered using one or more imaging modalities.

BACKGROUND

Traumatic brain injury (TBI) is a significant public health concern with annual costs estimated in the billions. In the United States alone, almost 1.7 million new cases of TBI present to emergency departments or require hospitalization each year. The gross majority (~75%) of TBI cases are classified as mild in severity with peak incidence in infants and young children and in late adolescence and early adulthood. Of the confirmed early and late adolescent TBIs, over 170,000 were due to sports and recreation. Within the range of mild TBI, it is reported that 15% will not have symptom resolution following a single mild brain injury. Thus, it is important to diagnose TBI as early as possible so that proper treatment plans can be adopted during the recovery process. Additionally, once diagnosed, it is important to track an individual's symptoms of TBI over time so that the treatment plans can be adjusted, as necessary.

Conventional systems of diagnosing TBI are directed to the quantification of symptoms of TBI. For example, these systems may determine the number and location of lesions on an individual's brain. However, there is no association between this information and the degree of severity. Accordingly, it is desired to produce a system for TBI assessment which provides for qualification of severity, along with quantification of related information.

SUMMARY

Embodiments of the present invention address and overcome one or more of the above shortcomings and drawbacks, by providing methods, systems, and apparatuses related to a modular and automated scoring system for traumatic brain injury (TBI) assessment. The disclosed technology may be used to assess TBI in a semi-automated fashion, using both automated segmentation and manual inputs from expert observers when needed. Those findings can be used and compared to a database of normal values in order to assess the extent and severity of the TBI, both in terms of structural damage and brain performance. Finally, a score is automatically established based on those indicators that reflect the global severity of the patient's TBI. This score can also be used to track disease evolution over time.

According to one aspect of the present invention, as described in some embodiments, a computer-implemented method for generating an assessment of traumatic brain injury (TBI) includes a TBI assessment computer receiving structural imaging data acquired by performing a structural imaging scan on an individual and generating a structural imaging score based on the structural imaging data. The TBI assessment computer receives functional imaging data acquired by performing a functional imaging scan on the individual and generates a functional imaging score based on the functional imaging data. The TBI assessment computer also receives diffusion imaging data acquired by performing a diffusion imaging scan on the individual and generates a diffusion imaging score based on the diffusion imaging data. Based on the structural imaging score, the functional imaging score, and the diffusion imaging score, the TBI assessment computer generates a TBI assessment score.

In some embodiments of the aforementioned method, the TBI assessment computer provides a graphical representation of the TBI assessment score in a graphical user interface. For example, in one embodiment, the TBI assessment computer generates an updated TBI assessment score based on an updated structural imaging score, an updated functional imaging score, and an updated diffusion imaging score. Then the TBI assessment computer may provide a graphical representation of the difference between the TBI assessment score and the updated TBI assessment score in the graphical user interface.

In some embodiments of the aforementioned method, the structural imaging data comprises first structural imaging data acquired using at least one of a T1 sequence and a T2-weighted sequence. In these embodiments, the method may further comprise determining a first score based on the first structural imaging data, wherein the structural imaging score is based on the first score. In one embodiment, the first score corresponds to prevalence of T2 hyper intensities within the first structural imaging data.

In some embodiments of the aforementioned method, the structural imaging data further comprises second structural imaging data acquired using at a Susceptibility-Weighted Imaging (SWI) sequence. In these embodiments, the method may then further comprise determining a second score based on the second structural imaging data, wherein the structural imaging score is further based on the second score. For example, in some embodiments, the second score corresponds to prevalence of lesions or masses within the second structural imaging data.

According to some embodiments of the aforementioned method, the functional imaging data is acquired using positron emission tomography (PET). In these embodiments, the method may then further comprise: identifying one or more lesion locations using the functional imaging data; and determining a third score based on the one or more lesion locations. The structural imaging score may then be further based on the third score. In one embodiment, the third score corresponds to prevalence of lesions or masses within the functional imaging data.

In some embodiments of the aforementioned method, the structural imaging data further comprises fourth structural imaging data acquired using a multi-component driven equilibrium single pulse observation of T1 and T2 (mcDESPOT) sequence. In these embodiments, the method may further include determining a fourth score based on the fourth structural imaging data, wherein the structural imaging score is further based on the fourth score. For example, in one embodiment, the fourth score corresponds to a comparison of the individual's deficient Myelin Water Fraction volume fraction (DVF) to DVF values associated with a plurality of normal subjects.

Additional features, refinements, or other enhancements may be made to the aforementioned method in different embodiments of the present invention. For example, in some embodiments, the functional imaging data comprises a plurality of functional images tracking changes in a brain region during an experiment. In some embodiments, the diffusion imaging data score corresponds to a comparison of a plurality of brain features present in the diffusion imaging data to corresponding brain features associated with a plurality of normal subjects. For example, in one embodiment, the brain features comprise: a tract length feature, a number of tracts feature, a symmetry of connectivity features, and one or more features corresponding to tensor map assessments.

According to another aspect of the present invention, as described in some embodiments, an article of manufacture for generating an assessment of TBI comprises a non-transitory, tangible computer-readable medium holding computer-executable instructions for performing the aforementioned method. This article of manufacture may further include instructions for any of the additional features discussed above with respect to the aforementioned method.

According to other embodiments of the present invention, a system for generating an assessment of TBI includes a data management component and a processor. The data management component is configured to receive: (i) structural imaging data acquired by performing a structural imaging scan on an individual; (ii) functional imaging data acquired by performing a functional imaging scan on the individual; and (iii) diffusion imaging data acquired by performing a diffusion imaging scan on the individual. The processor is configured to generate: (i) a structural imaging score based on the structural imaging data; (ii) a functional imaging score based on the functional imaging data; (iii) a diffusion imaging score based on the diffusion imaging data; and (iv) a TBI assessment score based on the structural imaging score, the functional imaging score, and the diffusion imaging score. In some embodiments, the system further includes a database which is configured to store the structural imaging data, the functional imaging data, and the diffusion imaging data.

The aforementioned processor may be configured with additional functionality in some embodiments. For example, in one embodiment the processor is further configured to generate an updated TBI assessment score based on an updated structural imaging score, an updated functional imaging score, and an updated diffusion imaging score. The processor may also provide a graphical representation of the difference between the TBI assessment score and the updated TBI assessment score in a graphical user interface on a display.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there are shown in the drawings embodiments that are presently preferred, it being understood, however, that the invention is not limited to the specific instrumentalities disclosed. Included in the drawings are the following Figures.

DETAILED DESCRIPTION

Systems, methods, and apparatuses are described herein which relate generally to a modular and automated scoring system for traumatic brain injury (TBI) assessment which utilizes structural, functional, and diffusion data acquired using one or more imaging modalities. The disclosed scoring system may be applied to any TBI analysis; however, it is especially applicable to mild TBI cases. Unlike moderate and severe TBI cases, mild TBI cases have traditionally proven very difficult to diagnose and characterize. One set of images is typically insufficient to properly identify and further characterize abnormalities caused by TBI. Structural information will give indicators of presence of lesions while functional and diffusion images will give degree of damage to the central nervous system, indicating how good the brain performs. Of course, while both sets of indicators can be related, it is possible not to have any findings or very few on structural and some in diffusion or functional measures. Therefore, the disclosed techniques utilize an automated algorithm that takes into account several imaging modalities and uses their specificity to combine findings into one score. This established score allows for assessment of the severity and extent of TBI and also provides means to tracking disease/behavior over time. This scoring model is also modular as from patient to patient, thus allowing the score to be adjusted if not all imaging modalities are available.

Figure 1:
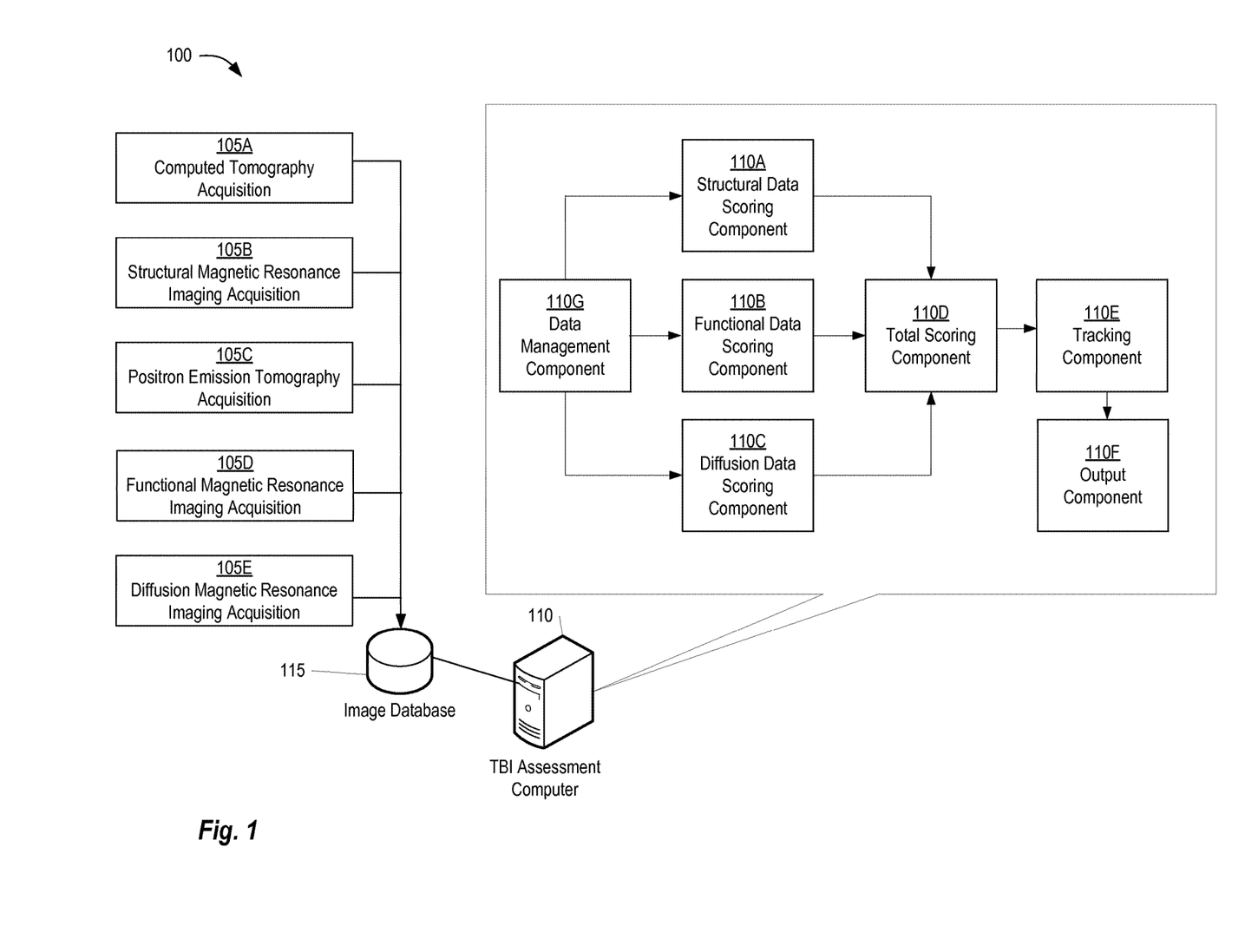
FIG. 1 provides an overview of a system that uses automated scoring for TBI assessment, according to some embodiments.

FIG. 1 provides an overview of a system 100 that uses automated scoring for TBI assessment, according to some embodiments. Briefly, imaging is performed on an individual using one or more imaging devices. In the example of FIG. 1, five types of image acquisitions are obtained: Computed Tomography Acquisition 105A, Structural Magnetic Resonance Imaging (MRI) Acquisition 105B, Positron Emission Tomography (PET) Acquisition 105C, Functional MRI Acquisition 105D, and Diffusion MRI Acquisition 105E. In some embodiments, these acquisitions 105A, 105B, 105C, 105D, and 105E may be obtained from two or more separate physical devices (e.g., imaging scanners). In other embodiments, a single device may provide data corresponding to multiple acquisitions depicted in FIG. 1. For example, the different MRI acquisitions depicted in FIG. 1 may be provided by a single scanner. All data from the acquisitions 105A, 105B, 105C, 105D, and 105E is stored in an Image Database 115. A TBI Assessment Computer 110 then uses the information stored in the Image Database 115 to generate a score representative of the individual's risk of TBI. In some embodiments, the Image Database 115 is part of the TBI Assessment Computer 110, while in other embodiments the Image Database 115 may be implemented on a separate computing device (not shown in FIG. 1). As an alternative to the use of the Image Database 115 as an intermediary storage mechanism, in some embodiments, data related to the acquisitions 105A, 105B, 105C, 105D, and 105E may be directly obtained and used as needed.

The data acquired from 105A, 105B, 105C, 105D, and 105E is used by three types of components within the TBI Assessment Computer 110: a Structural Data Scoring Component 110A, a Functional Data Scoring Component 110B, and Diffusion Data Scoring Component 110C. Each of these components 110A, 110B, and 110C generates scores for data of particular types. For example, the Structural Data Scoring Component 110A generates scores for data acquired via the Structural MRI Acquisition 105B. A Data Managements Component 110G coordinates the distribution of data between the Image Database 115 and the individual scoring components 110A, 110B, and 110C. This distribution may be performed based on, for example, the file types of the individual files stored in the image database or based on a preset association between the data source and a particular scoring component.

The Structural Data Scoring Component 110A generates scores using structural imaging data. Examples of structural imaging data that may be used by the Structural Data Scoring Component 110A include, without limitation, data from a Computed Tomography Acquisition 105A, a Structural MRI Acquisition 105B, and a Positron Emission Tomography (PET) Acquisition 105C. Each of these acquisitions 105A, 105B, and 105C may provide a variety of data related to their particular modality. For example, the Structural MRI Acquisition 105B may be used to acquire images using high resolution MR T1, T2-weighted, susceptibility-weighted imaging SWI, fluid-attenuated inversion recovery (FLAIR), and/or multi-component driven equilibrium single pulse observation of T1 and T2 (mcDESPOT) techniques.

In some embodiments, the Structural Data Scoring Component 110A is configured to identify lesions in the structural information provided by the various imaging modalities. In some embodiments, lesions are detected automatically by the Structural Data Scoring Component 110A during processing. In other embodiments, consensus markings from expert observers may be used for lesion detection. A confidence level may be configured based on the number of modalities/sequences that the lesions are detected on.

Figure 2:
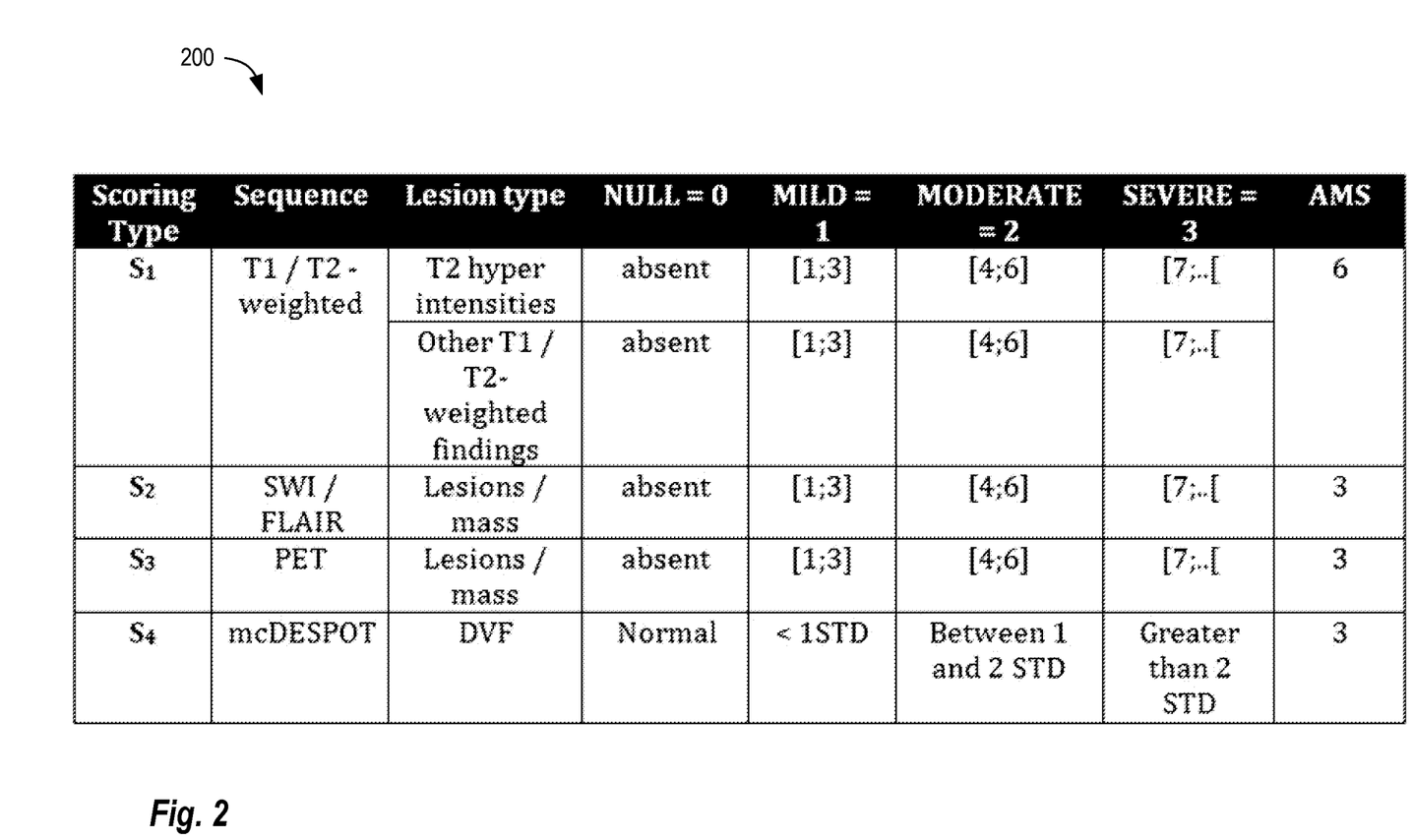
FIG. 2 provides a table showing an example of a structural data scoring system that may be employed in some embodiments.

FIG. 2 provides a table showing an example of a structural data scoring system 200 that may be employed by the Structural Data Scoring Component 110A in some embodiments. This scoring system 200 uses the number of lesions that are detected regardless of the modalities, and classifies them along brain regions (e.g., frontal, central, limbic, subcortical gray, parietal). The score for each of the lesion types is summed and the score for the whole brain is reflected by the maximum score among all the brain regions.

It should be noted that, in FIG. 2, Structural scoring is determined based on the number of sequences/modalities that are available for each patient. Thus, the scoring system 200 is applied to findings in T1/T2-weighted, SWI/FLAIR images, PET, and multi-component. In the example of FIG. 2, these sequences/modalities are ordered based on their likelihood to be available for TBI assessment. T1 and T2-weighted imaging data are the most likely to be present for such an assessment. This is represented for scoring type $S_1$ (Structural 1). The associated scoring value could then go up to 6. Scoring type $S_2$ represents both $S_1$ type sequences and SWI/FLAIR, with an associated maximum score (AMS) value of 9. Similarly, $S_3$ adds PET datasets into the existing scoring pool of data $S_2$ (AMS=12) and $S_4$ indicates that all categorized data are present in the assessment (AMS=15), including assessment of myelin in white matter, or mcDESPOT. As is understood in the art, mcDESPOT in combination with segmentation allows for additional derivation of Myelin Water Fraction (MWF) deficiency thanks to measures such as total deficient MWF volume or DV in White Matter (WM), in WM lesions, in diffusively abnormal WM and in normal appearing white matter (NAWM). Deficient MWF volume fraction (DVF) is derived from each of the above by dividing by the corresponding region volume. An individual's deficient MWF volume fraction is compared to those of a set of normal subjects and the scoring is based on how far apart from the statistically normal subjects the patient's DVF stands.

Figure 3:
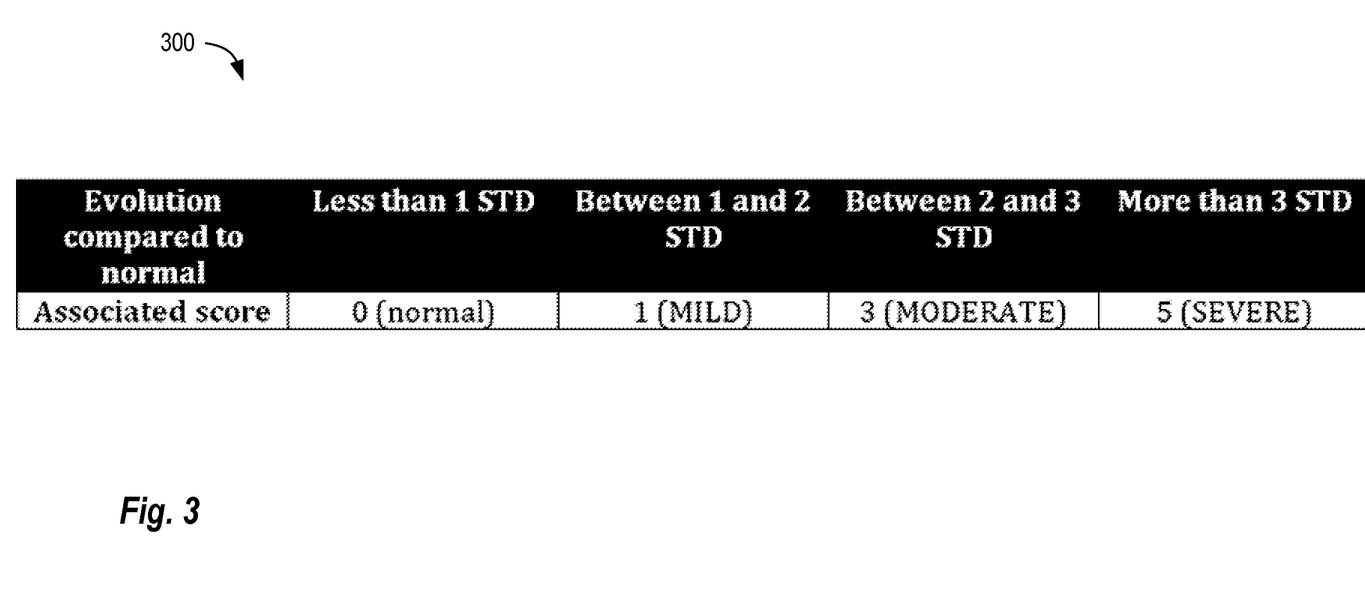
FIG. 3 provides a table illustrating an example functional data scoring system that may be employed in some embodiments.

Returning to FIG. 1, Functional Data Scoring Component 110B generates scores based on the availability of functional datasets (e.g., resting state fMRI) acquired from a Functional MRI Acquisition 105D. Using the functional data sets, the Functional Data Scoring Component 110B provides a measure of the deviation of the measurement from the expected normal values. For example, the patient data could be registered to the space of a normal subject and each voxel evolution over the course of the experiment would be compared to the normal. Evolution tracking could be performed, for example, within voxels or regions of interest (ROIs). The same could be done with functional data upon exercise, with a scoring methodology similar to that applied by the Structural Data Scoring Component 110A to structural data. For example, n>1 experiments may be performed and scored accordingly. Those experiments should be clearly defined and the data acquisitions standardized to increase the consistency of the score. FIG. 3 provides a table illustrating of an example functional data scoring system 300 that may be employed by the Functional Data Scoring Component 110B in some embodiments.

Figure 4:
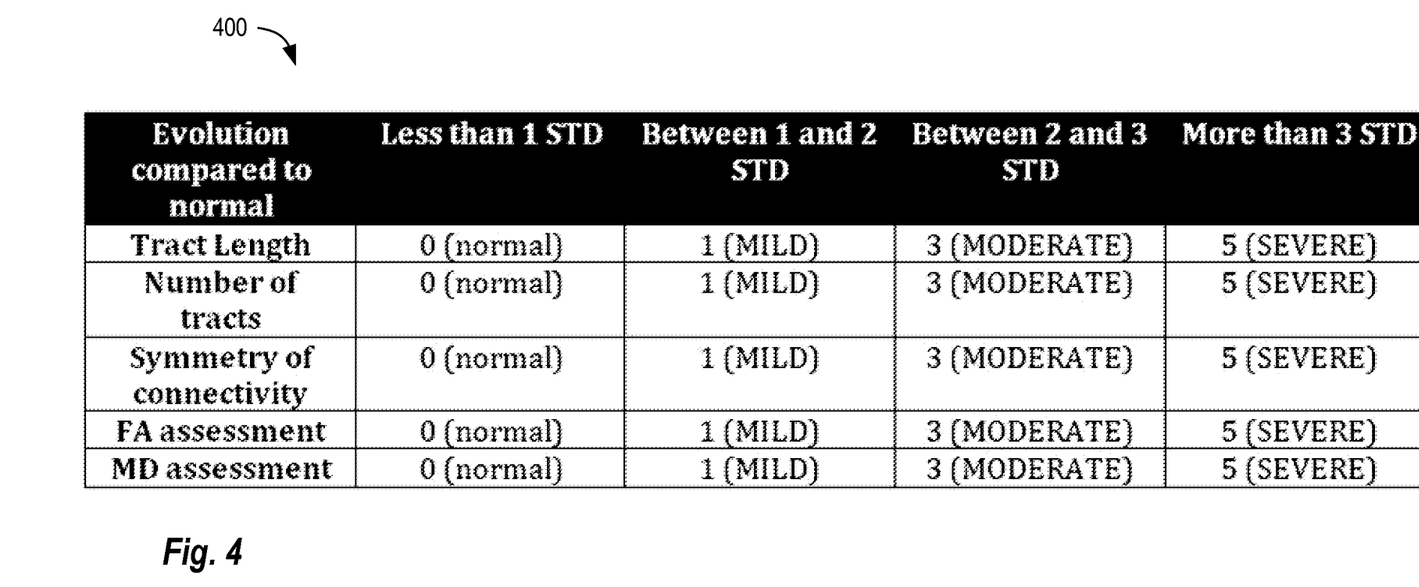
FIG. 4 provides a table illustrating a diffusion data scoring system that may be employed in some embodiments.

The Diffusion Data Scoring Component 110C generates scores based on diffusion data acquired from a Diffusion MRI Acquisition 105E. This diffusion data may be acquired, for example, using, diffusion tensor imaging, high-angular resolution diffusion imaging, and/or diffusion spectrum imaging techniques. The Diffusion Data Scoring Component 110C compares the diffusion data with scores from normal subjects accordingly. For diffusion scoring, there are a few features that can be taken into account. FIG. 4 provides a table illustrating a diffusion data scoring system 400 that may be employed by the Diffusion Data Scoring Component 110C in some embodiments. Scores in this example are determined by assessing several features using the white matter fiber tracts that are generated, via tractography, from diffusion models (e.g., diffusion tensors, orientation distribution functions, fiber orientation distributions, etc.), and are compared to their counterpart in normal subjects. The first row of the table presented in FIG. 4 references the feature of the length of the tracts, which can be compared to their average length in normal subjects. The second row of the table corresponds to the feature of the number of tracts going through specific regions of the brain. The third row of the table corresponds to the feature of symmetry of the connectivity (i.e., left vs right brain). Finally, the last two rows corresponds to assessments generated using tensor maps (fractional anisotropy (FA) and mean diffusivity (MD), respectively). For these two rows, the deviation from normal is compared (e.g., voxel-wise or average on brain ROIs).

Continuing with reference to FIG. 1, the Total Scoring Component 110D provides a global assessment of TBI by combining the different scores obtained as previously described. For example, in some embodiments, the global score is computed as follows:

$$TBIscore = K - (Struct.Score + Func.Score + Diff.Score)$$

K corresponds to a patient without any lesion or TBI. Thus, a lower score corresponds to a more severe TBI. K may be determined by the following equation:

$$K = K1 + \text{Max}_{structural} + \text{Max}_{functional} + \text{Max}_{diffusion}$$

K1 is used as a buffer to set a minimum non-zero score that may be determined based on experimental results or other a priori knowledge. For example, in some embodiments, K is set to 3. The value of $Max_{structural}$ will depend on the types of modality involved and may be determined using a summation of the AMS terms provided in FIG. 2 (i.e., $\Sigma_{i=1}^{n} AMS_i$). The value of $Max_{functional}$ represents the maximum functional score and may be set based on the scores employed for that type of data. For example, using the example scoring system 300 provided in FIG. 3, $Max_{functional}$ would be set to 5. Similarly, the value of $Max_{diffusion}$ represents the maximum diffusion score, based on the diffusion scoring information. For example, using the scoring system 400 presented in FIG. 4, a $Max_{diffusion}$ of 25 may be used (i.e., summing the maximum values for the 5 rows shown).

It should be noted that the maximum scoring calculation should match the overall scoring methodology. Thus, for example, a user may choose to only score one type of tract information in the diffusion data (e.g., symmetry of connectivity in FIG. 4). In this case, the $Max_{diffusion}$ would be 15, equal to the summation of the maximum values for symmetry of connectivity, FA assessment, and MD assesment, respectively.

A Tracking Component 110E receives and stores TBIScore from the Total Scoring Component 110D. Storage may be implemented, for example, using local storage in the TBI Assessment Computer 110 or on an external storage medium. In some embodiments, the TBI Assessment Computer 110 is configured to directly insert TBIScore into an Electronic Health Record (EHR) associated with the individual being scored. Additionally, in some embodiments, the Tracking Component 110E may be used to track changes to TBIScore over time. Thus, as new scans are acquired, new TBIScore values may be generated and compared to previously generated values. In this way, an individual's risk of TBI can be evaluated over a period following the injury. In some embodiments, the Tracking Component 110E may also provide statistics on changes to TBIScore over particular periods of time.

An Output Component 110F is used to deliver TBIScore to one or more external devices. For example, as explained above, in some embodiments, TBIScore is output to an EHR. In other embodiments, TBIScore may be presented in a graphical user interface (GUI), possibly with additional information such as a plot of how the TBI has changed over time. This GUI may also be used for displaying images used in generating TBIScore.

Figure 5:
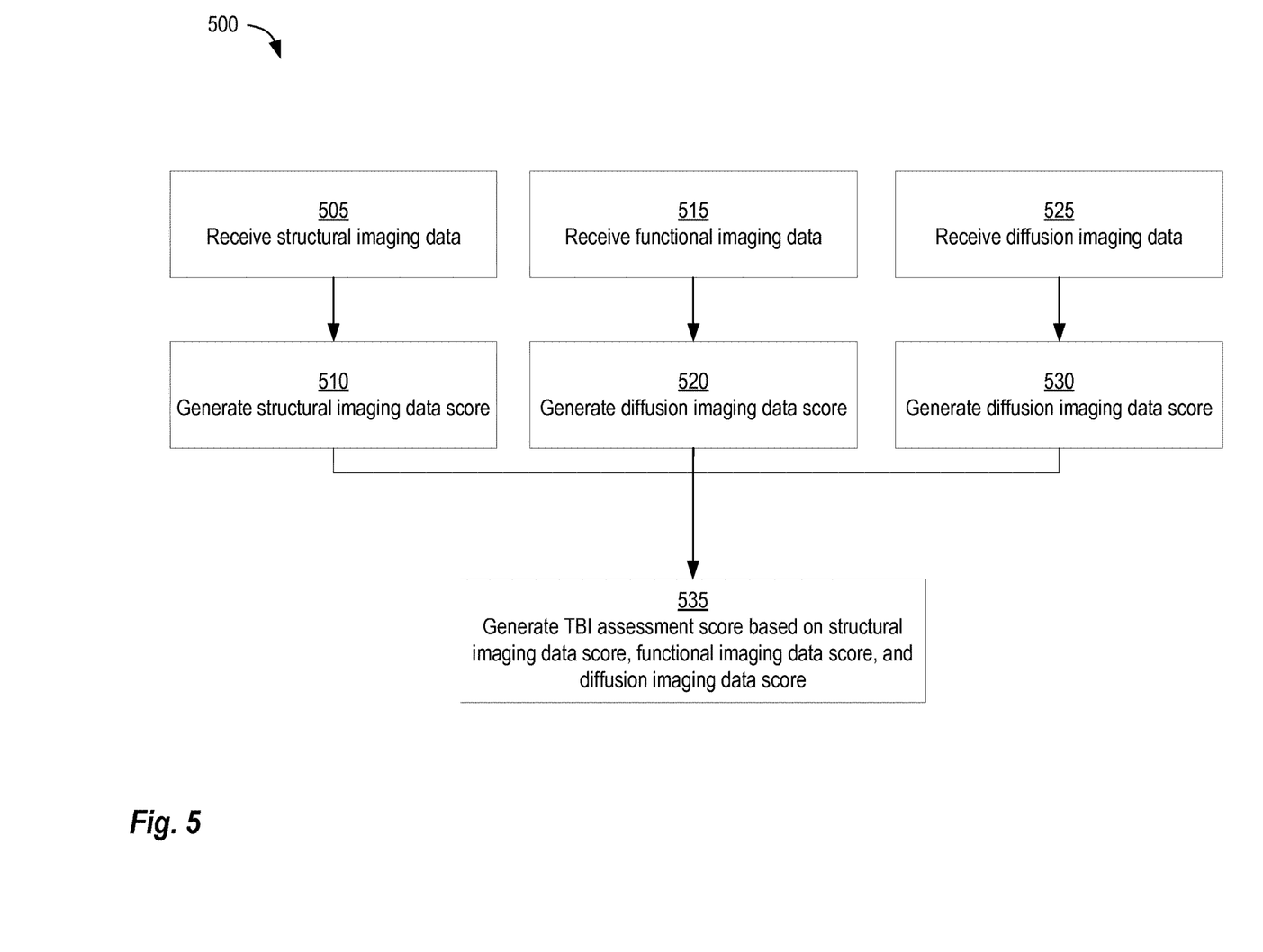
FIG. 5 provides a flow chart illustrating a method of implementing an automated scoring system for TBI assessment, according to some embodiments.

FIG. 5 provides a flow chart illustrating a method 500 of implementing an automated scoring system for TBI assessment, according to some embodiments. Briefly, FIG. 5 shows score generation for structural, functional, and diffusion imaging data. This score generation is performed in parallel across the various types of imaging data. It should be noted that the order of the steps presented in FIG. 5 is merely one example of how processing can occur. For example, various steps may be combined or performed in serial rather than parallel as illustrated in FIG. 5.

Starting at step 505, a TBI assessment computer (e.g., TBI Assessment Computer 110 in FIG. 1), receives structural imaging data acquired by performing a structural imaging scan on an individual. As explained above with reference to FIG. 1, this structural imaging scan may be performed using modalities such as, without limitation, MRI, CT, and PET. At step 510, the TBI assessment computer generates a structural imaging score based on the structural imaging data. For example, in some embodiments, the score is generated using the scoring system described above with reference to FIG. 2.

At steps 515-530, functional and diffusion data is processed in a manner similar to that described above with reference to the structural data. Thus, at step 515 the TBI assessment computer receives functional imaging data acquired by performing a functional imaging scan on the individual and, at step 520, the received data is used to generate a functional imaging score. Similarly, at step 525 the TBI assessment computer receives diffusion imaging data acquired by performing a diffusion imaging scan on the individual and, at step 530, the received data is used to generate a diffusion imaging score.

In some embodiments, various forms of each data type are processed simultaneously, while in other embodiments, data may be processed as available. For example, with reference to the structural data presented in FIG. 2, scores may be generated based on MRI data. At the same time, scores may be generated for PET data. Alternatively the PET data can be processed before the MRI data is even acquired. In this way, preliminary scores can be generated and refined as new data is acquired.

Continuing with reference to FIG. 5, at step 535, a TBI assessment score is calculated based on the structural imaging score, the functional imaging score, and the diffusion imaging score. In some embodiments, this score is then presented to the use in a GUI. Additionally the score may be stored to allow for tracking of TBI risk over time as new imaging is performed and new scores are generated.

Figure 6:
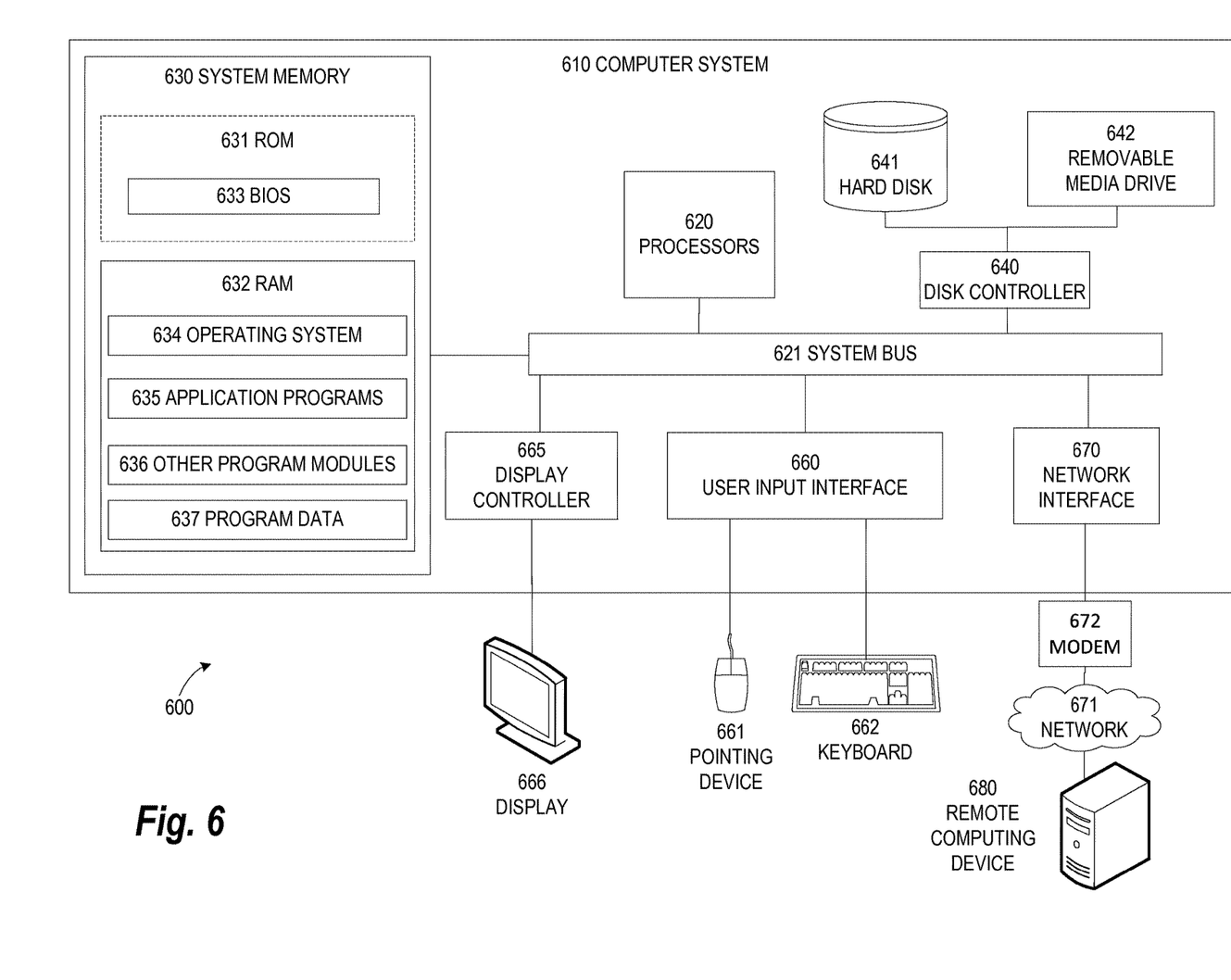
FIG. 6 illustrates an exemplary computing environment within which embodiments of the invention may be implemented.

FIG. 6 illustrates an exemplary computing environment 600 within which embodiments of the invention may be implemented. For example, computing environment 600 may be used to implement the TBI Assessment Computer 110 shown in FIG. 1. Computers and computing environments, such as computer system 610 and computing environment 600, are known to those of skill in the art and thus are described briefly here.

As shown in FIG. 6, the computer system 610 may include a communication mechanism such as a system bus 621 or other communication mechanism for communicating information within the computer system 610. The computer system 610 further includes one or more processors 620 coupled with the system bus 621 for processing the information.

The processors 620 may include one or more central processing units (CPUs), graphical processing units (GPUs), or any other processor known in the art. More generally, a processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and be conditioned using executable instructions to perform special purpose functions not performed by a general-purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

Continuing with reference to FIG. 6, the computer system 610 also includes a system memory 630 coupled to the system bus 621 for storing information and instructions to be executed by processors 620. The system memory 630 may include computer readable storage media in the form of volatile and/or nonvolatile memory, such as read only memory (ROM) 631 and/or random access memory (RAM) 632. The RAM 632 may include other dynamic storage device(s) (e.g., dynamic RAM, static RAM, and synchronous DRAM). The ROM 631 may include other static storage device(s) (e.g., programmable ROM, erasable PROM, and electrically erasable PROM). In addition, the system memory 630 may be used for storing temporary variables or other intermediate information during the execution of instructions by the processors 620. A basic input/output system 633 (BIOS) containing the basic routines that help to transfer information between elements within computer system 610, such as during start-up, may be stored in the ROM 631. RAM 632 may contain data and/or program modules that are immediately accessible to and/or presently being operated on by the processors 620. System memory 630 may additionally include, for example, operating system 634, application programs 635, other program modules 636 and program data 637.

The computer system 610 also includes a disk controller 640 coupled to the system bus 621 to control one or more storage devices for storing information and instructions, such as a magnetic hard disk 641 and a removable media drive 642 (e.g., floppy disk drive, compact disc drive, tape drive, and/or solid state drive). Storage devices may be added to the computer system 610 using an appropriate device interface (e.g., a small computer system interface (SCSI), integrated device electronics (IDE), Universal Serial Bus (USB), or FireWire).

The computer system 610 may also include a display controller 665 coupled to the system bus 621 to control a display or monitor 666, such as a cathode ray tube (CRT) or liquid crystal display (LCD), for displaying information to a computer user. The computer system includes an input interface 660 and one or more input devices, such as a keyboard 662 and a pointing device 661, for interacting with a computer user and providing information to the processors 620. The pointing device 661, for example, may be a mouse, a light pen, a trackball, or a pointing stick for communicating direction information and command selections to the processors 620 and for controlling cursor movement on the display 666. The display 666 may provide a touch screen interface that allows input to supplement or replace the communication of direction information and command selections by the pointing device 661.

The computer system 610 may perform a portion or all of the processing steps of embodiments of the invention in response to the processors 620 executing one or more sequences of one or more instructions contained in a memory, such as the system memory 630. Such instructions may be read into the system memory 630 from another computer readable medium, such as a magnetic hard disk 641 or a removable media drive 642. The magnetic hard disk 641 may contain one or more data stores and data files used by embodiments of the present invention. Data store contents and data files may be encrypted to improve security. The processors 620 may also be employed in a multi-processing arrangement to execute the one or more sequences of instructions contained in system memory 630.

In alternative embodiments, hard-wired circuitry may be used in place of or in combination with software instructions. Thus, embodiments are not limited to any specific combination of hardware circuitry and software.

As stated above, the computer system 610 may include at least one computer readable medium or memory for holding instructions programmed according to embodiments of the invention and for containing data structures, tables, records, or other data described herein. The term "computer readable medium" as used herein refers to any medium that participates in providing instructions to the processors 620 for execution. A computer readable medium may take many forms including, but not limited to, non-transitory, non-volatile media, volatile media, and transmission media. Non-limiting examples of non-volatile media include optical disks, solid state drives, magnetic disks, and magneto-optical disks, such as magnetic hard disk 641 or removable media drive 642. Non-limiting examples of volatile media include dynamic memory, such as system memory 630. Non-limiting examples of transmission media include coaxial cables, copper wire, and fiber optics, including the wires that make up the system bus 621. Transmission media may also take the form of acoustic or light waves, such as those generated during radio wave and infrared data communications.

The computing environment 600 may further include the computer system 610 operating in a networked environment using logical connections to one or more remote computers, such as remote computing device 680. Remote computing device 680 may be a personal computer (laptop or desktop), a mobile device, a server, a router, a network PC, a peer device or other common network node, and typically includes many or all of the elements described above relative to computer system 610. When used in a networking environment, computer system 610 may include modem 672 for establishing communications over a network 671, such as the Internet. Modem 672 may be connected to system bus 621 via user network interface 670, or via another appropriate mechanism.

Network 671 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 610 and other computers (e.g., remote computing device 680). The network 671 may be wired, wireless or a combination thereof. Wired connections may be implemented using Ethernet, Universal Serial Bus (USB), or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 671.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine-readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity. Also, while some method steps are described as separate steps for ease of understanding, any such steps should not be construed as necessarily distinct nor order dependent in their performance.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

We claim:

1. A computer-implemented method for generating an assessment of traumatic brain injury (TBI), the method comprising:
   receiving, by a TBI assessment computer, structural imaging data acquired by performing a structural imaging scan on an individual;
   generating, by the TBI assessment computer, a structural imaging numerical score based on the structural imaging data;
   receiving, by the TBI assessment computer, functional imaging data acquired by performing a functional imaging scan on the individual;
   generating, by the TBI assessment computer, a functional imaging numerical score based on the functional imaging data;
   receiving, by the TBI assessment computer, diffusion imaging data acquired by performing a diffusion imaging scan on the individual;
   generating, by the TBI assessment computer, a diffusion imaging numerical score based on the diffusion imaging data; and
   generating, by the TBI assessment computer, a TBI assessment numerical score by subtracting an ideal TBI assessment value from a summation of the structural imaging numerical score, the functional imaging numerical score, and the diffusion imaging numerical score,
   wherein the ideal TBI assessment value is determined based on a summation of a maximum possible structural imaging numerical score, a possible maximum functional imaging numerical score, and a maximum possible diffusion imaging numerical score.

2. The method of claim 1, further comprising:
   providing, by the TBI assessment computer, a graphical representation of the TBI assessment numerical score in a graphical user interface.

3. The method of claim 2, further comprising:
   generating, by the TBI assessment computer, an updated TBI assessment numerical score based on an updated structural imaging numerical score, an updated functional imaging numerical score, and an updated diffusion imaging numerical score;
   providing, by the TBI assessment computer, a graphical representation of the difference between the TBI assessment numerical score and the updated TBI assessment numerical score in the graphical user interface.

4. The method of claim 1, wherein the structural imaging data comprises first structural imaging data acquired using at least one of a T1 sequence and a T2-weighted sequence and the method further comprises:
   determining a first numerical score based on the first structural imaging data,
   wherein the structural imaging numerical score is based on the first numerical score.

5. The method of claim 4, wherein the first numerical score corresponds to prevalence of T2 hyper intensities within the first structural imaging data.

6. The method of claim 5, wherein the structural imaging data further comprises second structural imaging data acquired using at a Susceptibility-Weighted Imaging (SWI) sequence and the method further comprises:
   determining a second numerical score based on the second structural imaging data,
   wherein the structural imaging numerical score is further based on the second numerical score.

7. The method of claim 6, wherein the second numerical score corresponds to prevalence of lesions or masses within the second structural imaging data.

8. The method of claim 6, wherein the functional imaging data is acquired using positron emission tomography (PET) and the method further comprises:
   identifying one or more lesion locations using the functional imaging data;
   determining a third numerical score based on the one or more lesion locations,
   wherein the structural imaging numerical score is further based on the third numerical score.

9. The method of claim 8, wherein the third numerical score corresponds to prevalence of lesions or masses within the functional imaging data.

10. The method of claim 8, wherein the structural imaging data further comprises fourth structural imaging data acquired using a multi-component driven equilibrium single pulse observation of T1 and T2 (mcDESPOT) sequence and the method further comprises:
    determining a fourth numerical score based on the fourth structural imaging data,
    wherein the structural imaging numerical score is further based on the fourth numerical score.

11. The method of claim 10, wherein the fourth numerical score corresponds to a comparison of the individual's deficient Myelin Water Fraction volume fraction (DVF) to DVF values associated with a plurality of normal subjects.

12. The method of claim 1, wherein the functional imaging data comprises a plurality of functional images tracking changes in a brain region during an experiment.

13. The method of claim 1, wherein the diffusion imaging data numerical score corresponds to a comparison of a plurality of brain features present in the diffusion imaging data to corresponding brain features associated with a plurality of normal subjects.

14. The method of claim 13, wherein the brain features comprise:
   a tract length feature,
   a number of tracts feature,
   a symmetry of connectivity features, and
   one or more features corresponding to tensor map assessments.

15. An article of manufacture for generating an assessment of traumatic brain injury (TBI), the article of manufacture comprising a non-transitory, tangible computer-readable medium holding computer-executable instructions for performing a method comprising
   receiving structural imaging data acquired by performing a structural imaging scan on an individual;
   generating a structural imaging numerical score based on the structural imaging data;
   receiving functional imaging data acquired by performing a functional imaging scan on the individual;
   generating a functional imaging numerical score based on the functional imaging data;
   receiving diffusion imaging data acquired by performing a diffusion imaging scan on the individual;
   generating a diffusion imaging numerical score based on the diffusion imaging data; and
   generating a TBI assessment numerical score by subtracting an ideal TBI assessment value from a summation of the structural imaging numerical score, the functional imaging numerical score, and the diffusion imaging numerical score,
   wherein the ideal TBI assessment value is determined based on a summation of a maximum possible structural imaging numerical score, a possible maximum functional imaging numerical score, and a maximum possible diffusion imaging numerical score.

16. The article of manufacture of claim 15, wherein the method further comprises:
   providing a graphical representation of the TBI assessment numerical score in a graphical user interface.

17. The article of manufacture of claim 16, wherein the method further comprises:
   generating an updated TBI assessment numerical score based on an updated structural imaging numerical score, an updated functional imaging numerical score, and an updated diffusion imaging numerical score;
   providing a graphical representation of the difference between the TBI assessment numerical score and the updated TBI assessment numerical score in the graphical user interface.

18. A system for generating an assessment of traumatic brain injury (TBI), the system comprising:
   a processor configured to:
      generate a structural imaging numerical score based on the structural imaging data, acquired by performing a structural imaging scan on an individual,
      generate a functional imaging numerical score based on the functional imaging data, acquired by performing a functional imaging scan on the individual,
      generate a diffusion imaging numerical score based on the diffusion imaging data, acquired by performing a diffusion imaging scan on the individual, and
      generate a TBI assessment numerical score by subtracting an ideal TBI assessment value from a summation of the structural imaging numerical score, the functional imaging numerical score, and the diffusion imaging numerical score,
      wherein the ideal TBI assessment value is determined based on a summation of a maximum possible structural imaging numerical score, a possible maximum functional imaging numerical score, and a maximum possible diffusion imaging numerical score.

19. The system of claim 18, further comprising:
   a database configured to store the structural imaging data, the functional imaging data, and the diffusion imaging data.

20. The system of claim 19, wherein the processor is further configured to:
   generate an updated TBI assessment numerical score based on an updated structural imaging numerical score, an updated functional imaging numerical score, and an updated diffusion imaging numerical score; and
   provide a graphical representation of the difference between the TBI assessment numerical score and the updated TBI assessment numerical score in a graphical user interface on a display.

* * * * *